United States Patent
Sutor et al.

(10) Patent No.: US 7,607,036 B1
(45) Date of Patent: Oct. 20, 2009

(54) SYSTEM AND METHOD FOR ENABLING CONTINUED USE OF TRIM VALUES WITHIN AN IMPLANTABLE MEDICAL DEVICE FOLLOWING A PARITY ERROR

(75) Inventors: Jason Sutor, Sunnyvale, CA (US); Renjie Huang, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 599 days.

(21) Appl. No.: 11/423,615

(22) Filed: Jun. 12, 2006

(51) Int. Cl.
G06F 11/20 (2006.01)

(52) U.S. Cl. ............................. 714/6; 607/59; 714/805

(58) Field of Classification Search .................. 714/6, 714/805; 607/59
See application file for complete search history.

(56) References Cited

U.S. PATENT DOCUMENTS

| | | | |
|---|---|---|---|
| 5,571,141 A | 11/1996 | McNeil et al. | |
| 5,607,458 A | 3/1997 | Causey, III et al. | |
| 5,653,735 A | 8/1997 | Chen et al. | |
| 5,735,882 A * | 4/1998 | Rottenberg et al. | 607/27 |
| 5,792,201 A | 8/1998 | Causey, III et al. | |
| 6,282,450 B1 * | 8/2001 | Hartlaub et al. | 607/59 |
| 6,532,389 B1 | 3/2003 | Shahandeh | |
| 6,635,048 B1 * | 10/2003 | Ullestad et al. | 604/890.1 |
| 6,662,049 B1 * | 12/2003 | Miller | 607/27 |
| 7,160,284 B2 * | 1/2007 | Ullestad et al. | 604/891.1 |

\* cited by examiner

*Primary Examiner*—Stephen M Baker
(74) *Attorney, Agent, or Firm*—Steven M. Mitchell; Theresa A. Takeuchi

(57) ABSTRACT

Techniques are described for use by an implantable medical device equipped to use trim values, which allow the device to continue to use trim values despite certain memory errors such as parity errors. Briefly, optimal trim values are stored within RAM. Nominal trim values are stored within ROM. Device functions are then performed using the trim values stored within RAM. If an error is detected indicative of possible corruption of RAM, then the trim values from ROM are loaded into RAM to enable continued operation of the device using the nominal trim values despite the error. In a preferred implementation, the optimized trim values are initially stored at two separate locations within RAM. A procedure is described herein for allowing the device to continue to use the optimized trim values following a device reset if no parity error is detected. If a parity error occurred, the device instead uses the nominal trim values from ROM.

15 Claims, 5 Drawing Sheets

SYSTEM AND METHOD FOR ENABLING CONTINUED USE OF TRIM VALUES WITHIN AN IMPLANTABLE MEDICAL DEVICE FOLLOWING A PARITY ERROR

FIELD OF THE INVENTION

The invention generally relates to implantable medical devices and, in particular, to techniques for using trim values within such devices.

BACKGROUND OF THE INVENTION

A wide variety of implantable medical devices are provided for surgical implantation into humans or animals. One common example is the cardiac pacemaker. Another is the implantable cardioverter defibrillator (ICD). State of the art implantable medical devices often include a programmable microcontroller for controlling the functions of the device to detect medical conditions within the patient in which the device is implanted and to control delivery of appropriate therapy. Within a pacemaker, for example, the microcontroller monitors the detection of P-waves and R-waves within electrical heart signals to determine whether an arrhythmia has occurred and, if so, controls a pulse generator to generate pacing pulses for delivery to the heart. Within an ICD, for example, the microcontroller analyzes P-waves, R-waves and other electrical signals of the heart to determine if an episode of atrial or ventricular fibrillation has occurred and, if so, controls a shocking circuit to generate shocks for delivery to the heart. In addition to performing functions directed to deliver of therapy, the microcontroller coordinates all other functions of the implanted device such as: switching of the mode of operation of the device from, for example, a single-chambered pacing mode to a dual-chambered pacing mode and recording events such as detection of P-waves and R-waves for diagnostic purposes.

The microcontroller uses a wide variety of parameters while performing its various functions. One set of parameters are device trim values, which are provided by the manufacturer to account for variations in tolerances or components arising during manufacture or assembly. For example, some trim values are correction factors for voltage measurements; others define the size of the random access memory (RAM) installed in the device. Trims are typically set to different values for different models and, in some cases, are set to different values for different units of the same model. For example, different models from the same manufacturer may be equipped to perform different functions requiring different trim values. The trim values are set by the manufacturer so as to help the device operate as closely to the design ideals as possible. In some cases, different units of the same model may be assembled using components from different suppliers, thus requiring slightly different trim values. Even when using the same components from the same suppliers, slight variations can nevertheless arise during assembly. Hence, the trim values are preferably optimized for each particular unit. Typically, automatic testing equipment (ATE) is used to test each individual unit following assembly and to then set the device trims for that individual unit accordingly. Usually, the trim values are loaded into RAM within the device by the ATE. Once the trims are set by the ATE, the trims are typically not changed.

Problems, however can arise in connection with trim values stored in RAM in the event of a parity error (i.e. a bit flip). If a parity error occurs in RAM, then every time that memory location is accessed by software of the microcontroller, the software "resets", preventing the implanted device from functioning properly. Parity errors can typically be corrected merely by reloading the correct data into the RAM address where the parity error occurred—so long as the correct data can be obtained. For many types of data used by an implantable device, nominal values for the data may be retrieved from read only memory (ROM). If so, the device can correct the parity error automatically and continue functioning. For example, ROM may store nominal or default values for various pacing parameters such as base rate, rest rate, etc. In other cases, however, the correct data must be reloaded into the implanted device by an external system, such as a device programmer. This typically may be achieved via remote telemetry so that the device need not be removed from the patient. However, with trim values, the correct trim values for a given device are set by the ATE of the manufacturer and hence can vary from unit to unit. As such, the correct trim values for a given unit are not stored in ROM and are available via an external programmer. Indeed, even the manufacturer may not have a record of trim values originally stored within the RAM of a given unit. Hence, if a parity error occurs within a portion of RAM where trim values are stored, that parity error typically cannot be corrected. The device therefore can no longer use trim values. If the device requires the trim values to operate, the device must then be removed and replaced, at considerable cost, inconvenience and risk.

As can be appreciated, there is a significant need to provide a reliable technique for handling parity errors within trim value memory and it is to this end that the invention is primarily directed.

SUMMARY OF THE INVENTION

In accordance with the invention, techniques are provided for use by an implantable medical device equipped to use trim values, which allow the device to continue to use trim values despite certain memory errors such as parity errors. Briefly, a first set of trim values are stored within RAM. A second, different set of trim values are stored within ROM. Device functions are then performed using the trim values stored within RAM. If an error is detected indicative of possible corruption of RAM, then the trim values from ROM are loaded into RAM to enable continued operation of the device using the ROM trim values despite the error. Preferably, the first set of trim values are optimized trim values provided by an ATE for use with a particular device from a particular manufacturer. The second set of trim values are nominal trim values appropriate for use, for example, with all devices of a particular model provided by the manufacturer.

In a preferred implementation, the optimized trim values are initially stored at two separate locations within RAM. Device software accesses the first of those locations to obtain the trim values to use during operation of the device. If a software reset is then detected, the device software determines whether the reset was due to a parity error in the RAM containing the trim values. If the reset was due to a parity error, then the nominal trim values are loaded from ROM into the first set of RAM locations so as to enable continued operation of the device using the nominal trim values despite the parity error. On the other hand, if the reset was not due to a parity error, then the optimized trim values from the second set of RAM locations are loaded into the first set of RAM locations so as to enable continued operation of the device using optimized trim values. Hence, in either case, the device can continue to use trim values—either optimized values or, at least, nominal values.

The invention may be advantageously implemented in pacemakers, ICDs or other implantable medical devices.

BRIEF DESCRIPTION OF THE DRAWINGS

Further features and advantages of the invention may be more readily understood by reference to the following description taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the descriptions that follow, like numerals or reference designators are used to refer to like parts or elements throughout.

Trim Value Reset Technique

Figure 1:
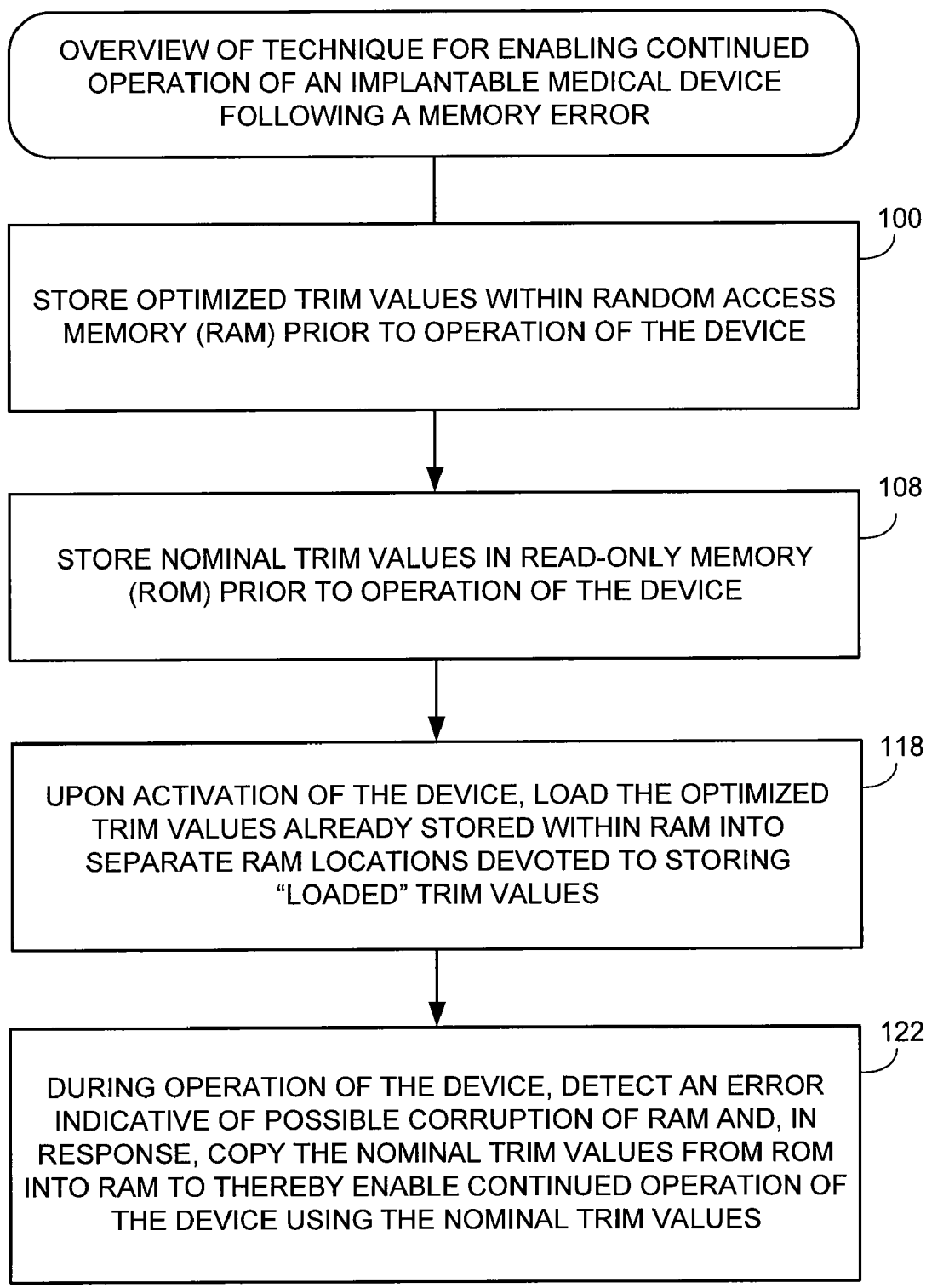
FIG. 1 provides an overview of the trim value reset technique of the invention for use with an implantable medical device.
Figure 2:
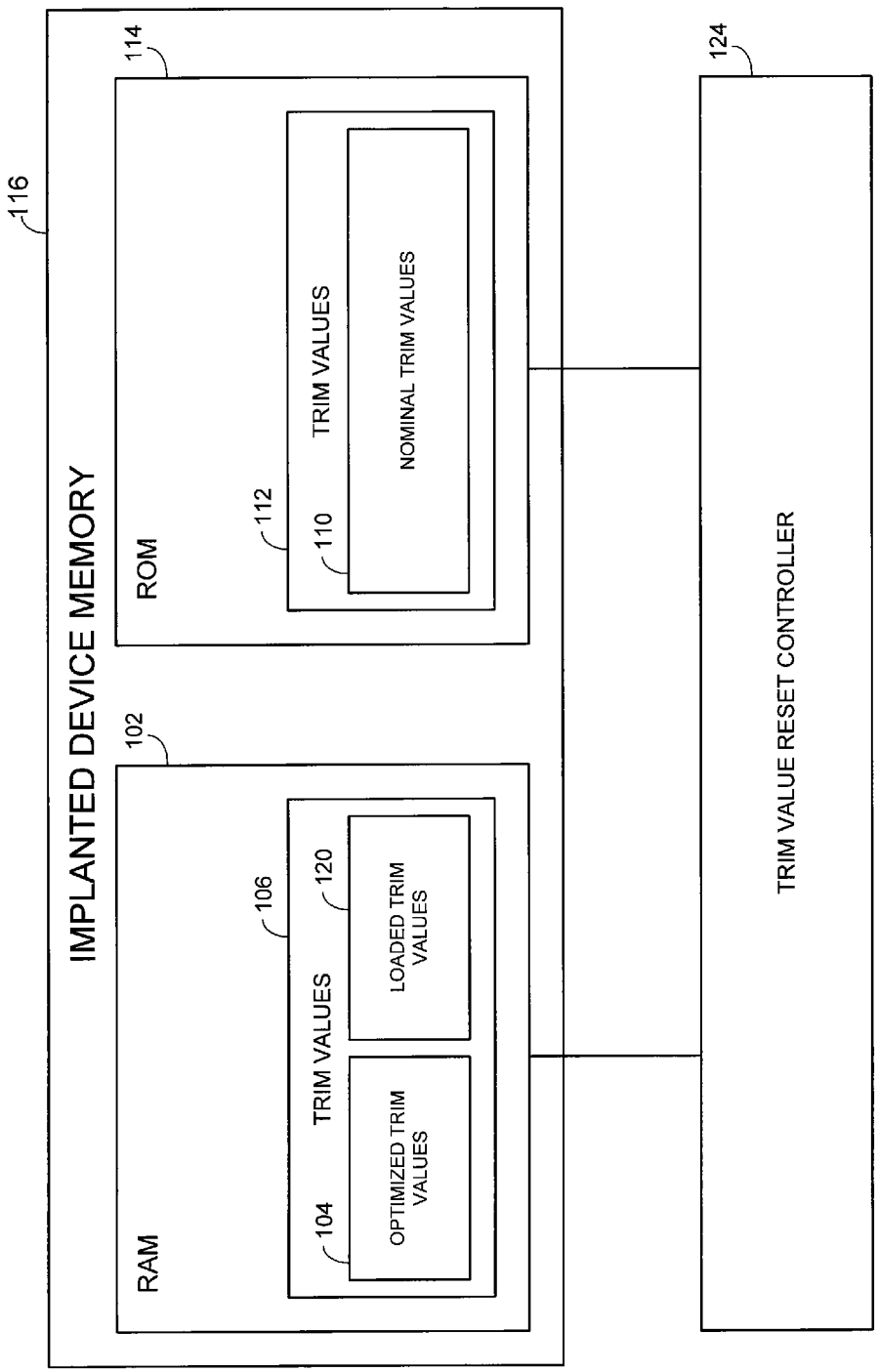
FIG. 2 is a block diagram illustrating pertinent portions of a memory of an exemplary implantable medical device subject to the general technique of FIG. 2.

FIG. 1 provides an overview of a trim value reset technique for use with an implantable medical device memory system such as the one illustrated in FIG. 2. Initially, at step 100, prior to operation of the medical device, optimized trim values are stored within a random access memory (RAM) 102 of the device. More specifically, optimized trim values are stored within a first set of memory locations 104 within a trim value portion 106 of RAM 102. The optimized trim values are also referred to herein as the first set of trim values and represent preferred or optimal trim values for use with the particular device, obtained through otherwise conventional engineering techniques by the manufacturer. Typically, these values are stored in RAM by the manufacturer following device assembly and before the device is shipped to a physician for implant. For example, an ATE may be used to test each individual unit following assembly and to then set the device trims for that individual unit accordingly. At step 108, also prior to the operation of the device, nominal trim values 110 are stored in a trim value portion 112 of read-only memory (ROM) 114. The nominal trim values are also referred to herein as the second set of trim values and represent trim values that may not be optimal but are nevertheless acceptable values for use with the device. Nominal trim values are also obtained through otherwise conventional engineering techniques. Typically, these values are stored in ROM by the manufacturer during device assembly or manufacture. Collectively, RAM 102 and ROM 114 comprise the memory 116 of the implanted device. As can be appreciated, a wide variety of other data and programs are stored within other portions of memory 116, including the various programs that control the functions and operations of the implanted device.

At step 118, upon activation of the implanted device, the optimized trim values 104 are loaded into separate locations 120 within RAM 102 devoted to storing loaded trim values, also referred to herein as the second set of RAM locations. This step is performed, typically, when the software of the implanted device is booted up, prior to implant. Hence, following step 118, first and second memory locations 104 and 120 of RAM 102 both store the same values—the optimized trim values. Thereafter, during operation of the implanted device, at step 122, an error indicative of a possible corruption of data in the RAM is detected and, in response, the nominal trim values 110 are copied from ROM 114 into the loaded trim value storage locations 120 of RAM 102 to thereby enable continued operation of the implanted device using the nominal trim values. This may be performed under the control of a reset controller 124, referred to herein as a trim value reset controller, or other appropriate device for handling software resets. Although shown as being a separate component from device memory 116, the reset controller may be configured as a control program hardwired into ROM 114. In any case, by loading the nominal trim values into locations 120 within RAM, the implanted device can still continue to operate reliably, though using nominal trim values rather than the optimized trim values. More specifically, once the device software begins running again following the reset, the software will automatically retrieve the trim values from memory locations 120 of the RAM.

Figure 3:
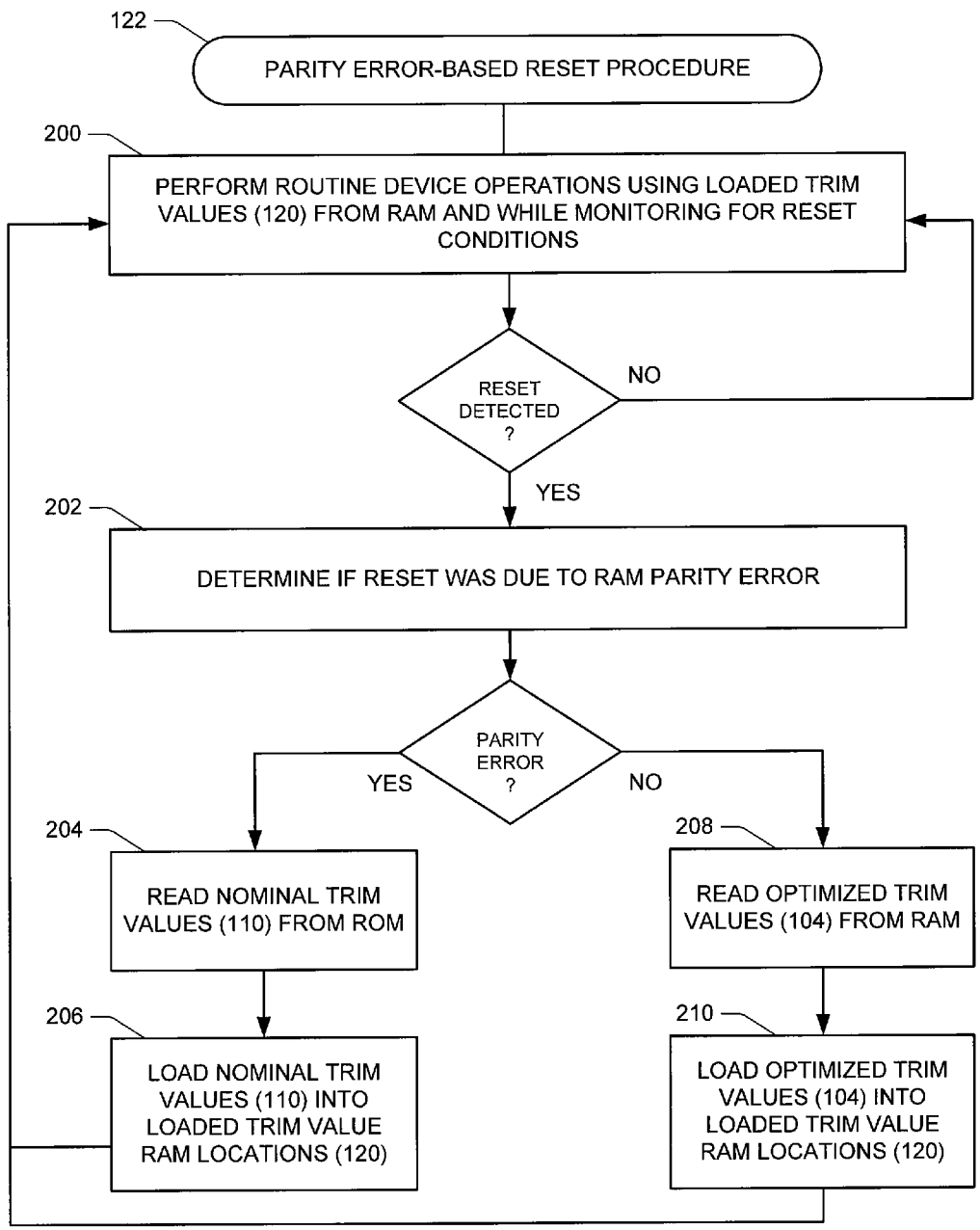
FIG. 3 is a flow chart illustrating a particular exemplary correction technique performed in accordance with the general technique of FIG. 1.

FIG. 3 illustrates a preferred implementation wherein transfer of the nominal trim value from ROM into RAM is only performed in circumstances where the reset was due to a parity error. During step 200, the implanted device performs all routine functions (sensing, pacing, etc.) using the optimized trim values loaded into RAM while monitoring for software reset conditions. A reset may occur, for example, if a significant software error occurs. If a reset is detected, then, at step 202, the implanted device determines whether the reset was due to a RAM parity error. This may be achieved by performing an otherwise conventional parity test on the RAM under the control of a software reset controller or other suitable device. If a parity error has occurred, then step 204 is performed wherein nominal trim values are retrieved from ROM and then loaded, at step 206, into RAM locations 120 (as has already described in connection with FIG. 1). However, if no parity error is detected, then steps 208 and 210 are instead performed, wherein the optimized trim values are retrieved from RAM memory locations 104 (FIG. 1) and then loaded into the loaded trim value RAM locations 120 (also FIG. 1.) In this manner, the device can continue to use the optimized trim values following any software reset not involving a RAM parity error. In this regard, if no parity error is detected, then it can reasonably be assumed that trim values in RAM have not been corrupted and can still be used. The nominal trim values are instead used only in the event of a parity error where there is a significant risk that the trim values in RAM have been corrupted.

What have been described are various techniques for responding to memory errors within the memory of an implantable medical device. For the sake of completeness, a detailed description of an exemplary pacer/ICD for performing these functions will now be provided. However, principles of invention may be implemented within other pacer/ICD implementations or within other implantable devices.

Exemplary Pacemaker/ICD

Figure 4:
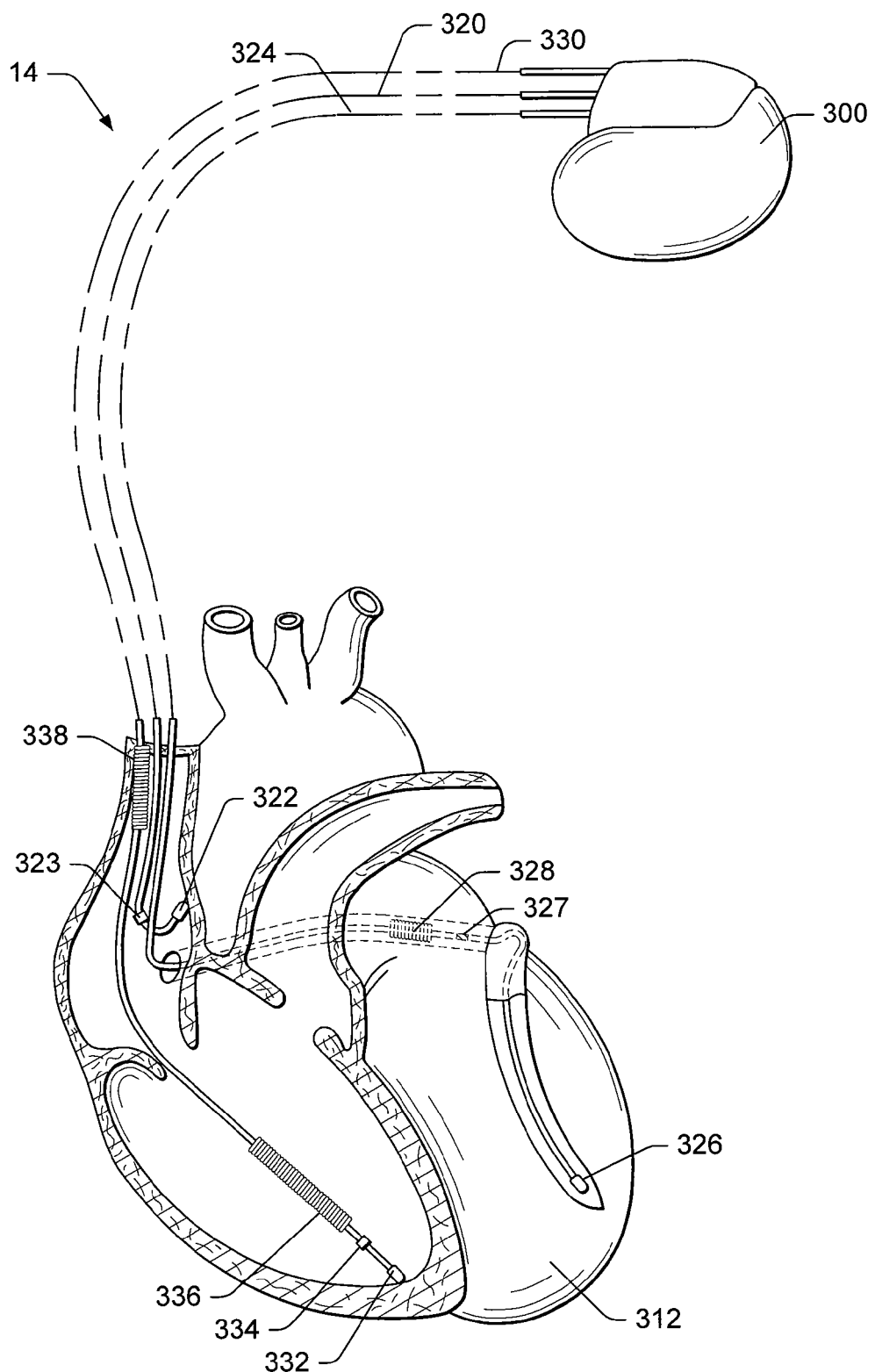
FIG. 4 is a simplified, partly cutaway view, illustrating an exemplary pacer/ICD, in which the trim reset techniques of FIGS. 1-3 can be implemented, along with a set of exemplary leads implanted in the heart of the patient.

FIG. 4 provides a simplified diagram of a pacer/ICD 10, which is a multi-chamber stimulation device capable of treating both fast and slow arrhythmias with stimulation therapy, including cardioversion, defibrillation, and pacing stimulation (as well as capable of tracking respiration, detecting episodes of abnormal respiration and delivering appropriate therapy.) To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 5:
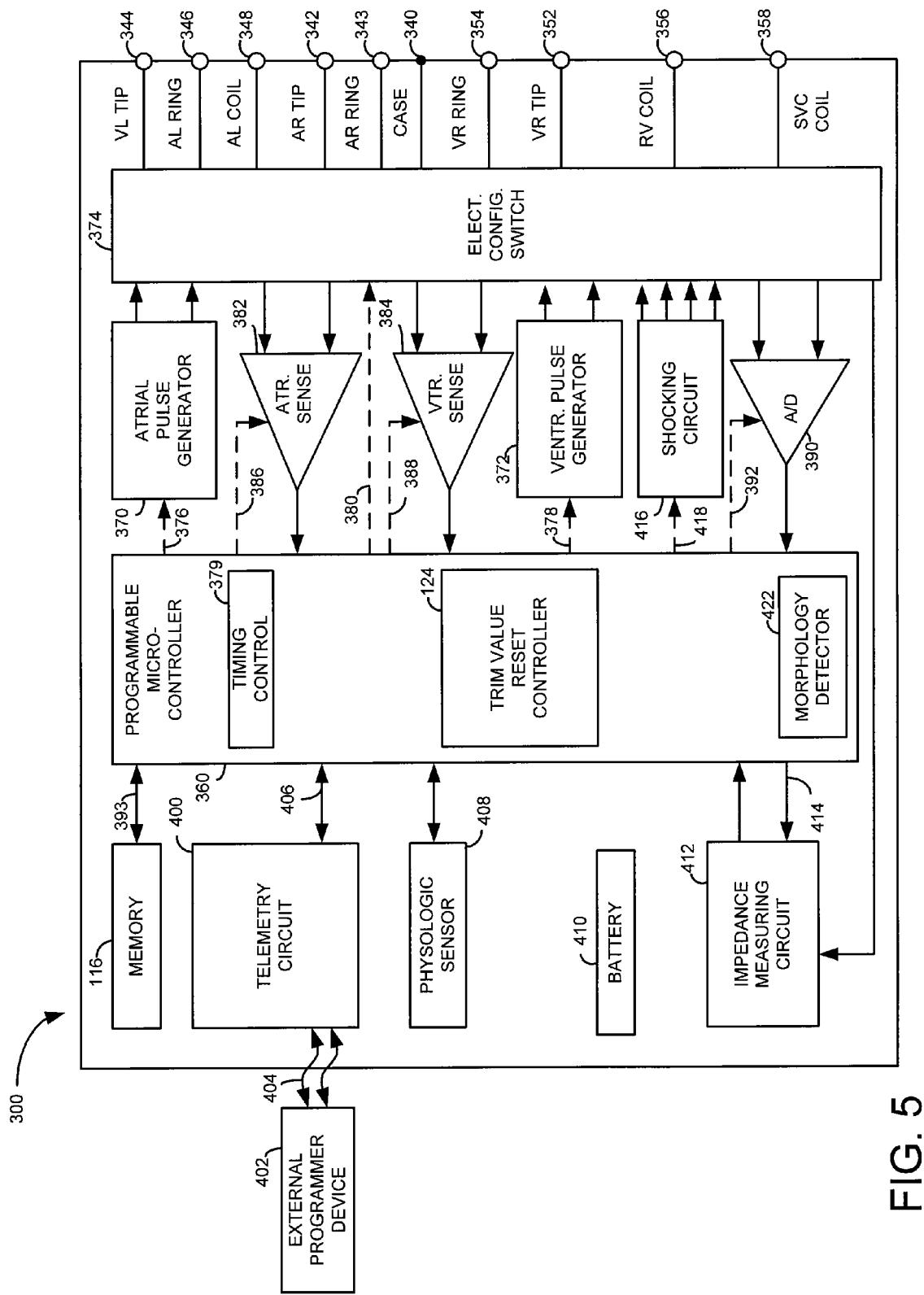
FIG. 5 is a functional block diagram of the pacer/ICD of FIG. 4, illustrating basic circuit elements that provide cardioversion, defibrillation and/or pacing stimulation in four chambers of the heart and particularly illustrating components for performing a trim value reset procedure.

A simplified block diagram of internal components of pacer/ICD 10 is shown in FIG. 5. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 340 for pacer/ICD 10, shown schematically in FIG. 5, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 343. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

Microcontroller 360 also includes the trim value reset controller 124 of FIG. 2 for controlling the operations described above in connection with FIGS. 1-3. Depending upon the implementation, the trim value reset controller may be implemented separately from the microcontroller.

As shown in FIG. 5, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 300 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 300 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 116 by a suitable data/address bus 396, wherein the programmable operating parameters used by the microcontroller 360 are stored and modified, as required, in order to customize the operation of pacer/ICD 300 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy.

Other pacing parameters include base rate, rest rate and circadian base rate. Parity errors within the memory are detected and Advantageously, the operating parameters of the implantable pacer/ICD 300 may be non-invasively programmed into the memory 116 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 300 (as contained in the microcontroller 360 or memory 116) to be sent to the external device 402 through an established communication link 404. Pacer/ICD 300 further includes an accelerometer or other physiologic sensor 408, commonly referred to as a "rate-responsive" sensor because it is typically used to adjust pacing stimulation rate according to the exercise state of the patient. However, the physiological sensor 408 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 300, it is to be understood that the sensor 408 may also be external to pacer/ICD 300, yet still be implanted within or carried by the patient. A common type of rate responsive sensor is an activity sensor incorporating an accelerometer or a piezoelectric crystal, which is mounted within the housing 340 of pacer/ICD 300. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 5. The battery 410 may vary depending on the capabilities of pacer/ICD 300. If the system only provides low voltage therapy, a lithium iodine or lithium copper fluoride cell may be utilized. For pacer/ICD 300, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, pacer/ICD 300 is preferably capable of high voltage therapy and batteries or other power sources appropriate for that purpose are employed.

As further shown in FIG. 5, pacer/ICD 300 is shown as having an impedance measuring circuit 412 which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 374 so that any desired electrode may be used.

In the case where pacer/ICD 300 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

The various functional components of the exemplary system may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to."

The invention claimed is:

1. A method for use with an implantable medical device equipped to use trim values, the method comprising:
   storing a first set of trim values within a random access memory (RAM) of the device;
   storing a second, different set of trim values within a read-only memory (ROM) of the device;
   performing device functions using the trim values stored within RAM; and
   detecting an error indicative of possible corruption of RAM and, in response, loading the trim values from ROM into RAM to enable continued operation of the device using trim values despite the error, wherein storing the first set of trim values within the first set of memory locations within RAM is performed by automatic test equipment (ATE) of the manufacturer following a test of the properties of the particular device.

2. A method for use with an implantable medical device equipped to use trim values, the method comprising:
   storing a first set of trim values within a random access memory (RAM) of the device;
   storing a second, different set of trim values within a read-only memory (ROM) of the device;
   performing device functions using the trim values stored within RAM; and
   detecting an error indicative of possible corruption of RAM and, in response, loading the trim values from ROM into RAM to enable continued operation of the device using trim values despite the error, wherein detecting an error indicative of possible corruption of RAM includes detecting a software reset and then determining whether the software reset was due to a parity error in RAM.

3. The method of claim 2 wherein the steps of storing the first set of trim values within the first set of memory locations within RAM and storing the second, different set of trim values within the ROM are both performed prior to initial activation of the device.

4. The method of claim 2 wherein the first set of trim values are initially stored both in first and second memory locations within RAM and wherein device functions are performed using the trim values stored within the first set of RAM locations.

5. The method of claim 4 wherein
   if the software reset was due to a parity error, then the trim values from ROM are loaded into the first set of RAM locations to enable continued operation of the device using the second set of trim values; and
   if the software reset was not due to a parity error, then the trim values from the second set of RAM locations are loaded into the first set of RAM locations to enable continued operation of the device using the first set of trim values.

6. The method of claim 2 wherein the first set of trim values stored in RAM are optimized trim values optimized for use with a subset of devices provided by a particular manufacturer and wherein the second set of trim values stored in ROM are nominal trim values appropriate for use with any of a larger set of devices provided by the same manufacturer.

7. The method of claim 6 wherein the first set of trim values stored in RAM are optimized for the particular device and wherein the second set of trim values stored in ROM are appropriate for all devices of the same model provided by the same manufacturer.

8. A method for use with an implantable medical device having memory equipped to store trim values, the method comprising:
   storing optimized trim values at trim value memory locations within random access memory (RAM) prior to operation of the device;
   storing nominal trim values in read-only memory (ROM) prior to operation of the device;
   upon activation of the device, loading the optimized trim values into separate RAM locations devoted to storing loaded trim values;
   performing device functions using the loaded trim values under the control of device software;
   detecting a software reset during operation of the device;
   determining, in response, whether a parity error occurred in RAM;
   if a parity error occurred, then loading the nominal trim values from ROM into the separate RAM locations devoted to storing loaded trim values to enable continued operation of the device using the nominal trim values despite the parity error; and
   if a parity error did not occur, then reloading the optimized trim values from RAM into the separate RAM locations devoted to storing loaded trim values to enable continued operation of the device using optimized trim values.

9. A method for use with an implantable medical device equipped to use trim values and having a random access memory (RAM) storing a first set of trim values and having a read-only memory (ROM) storing a second, different set of trim values, the method comprising:
   performing device functions using the trim values stored within RAM; and detecting an error indicative of possible corruption of RAM and, in response, loading the trim values from ROM into RAM to enable continued operation of the device using the ROM trim values despite the error.

10. A system for use with an implantable medical device equipped to utilize trim values, the system comprising:
random access memory (RAM) operative to store a first set of trim values;
read-only memory (ROM) operative to store a second set of trim values; and
a trim value reset controller operative to detect an error indicative of possible corruption of RAM and, in response, loading the trim values from ROM into RAM to enable continued operation of the device using the ROM trim values despite the error, wherein the trim value reset controller is operative to detect an error indicative of possible corruption of RAM by detecting a software reset and then determining whether the software reset was due to a parity error in RAM.

11. The system of claim 10 wherein the first set of trim values are stored both in first and second memory locations within RAM and wherein device functions are performed using the trim values stored within the first set of RAM locations.

12. The system of claim 11 wherein
if the software reset was due to a parity error, then the trim value reset controller loads the trim values from ROM into the first set of RAM locations to enable continued operation of the device using the second set of trim values; and
if the software reset was not due to a parity error, then the trim value reset controller instead loads trim values from the second set of RAM locations into the first set of RAM locations to enable continued operation of the device using the first set of trim values.

13. The system of claim 10 wherein the first set of trim values stored in RAM are optimized trim values optimized for use with a subset of devices provided by a particular manufacturer and wherein the second set of trim values stored in ROM are nominal trim values appropriate for use with any of a larger set of devices provided by the same manufacturer.

14. The system of claim 13 wherein the first set of trim values stored in RAM are optimized for the particular device and wherein the second set of trim values stored in ROM are appropriate for all devices of the same model provided by the same manufacturer.

15. A system for use with an implantable medical device equipped to utilize trim values, the system comprising:
means for storing a first set of trim values within a random access memory (RAM) of the device;
means for storing a second set of trim values within a read-only memory (ROM) of the device; and
means for detecting an error indicative of possible corruption of RAM by detecting a software reset;
means for determining whether the software reset was due to a parity error in RAM and,
means for loading the trim values from ROM into RAM to enable continued operation of the device using the ROM trim values despite the error.

* * * * *

UNITED STATES PATENT AND TRADEMARK OFFICE
CERTIFICATE OF CORRECTION

PATENT NO. : 7,607,036 B1  Page 1 of 1
APPLICATION NO. : 11/423615
DATED : October 20, 2009
INVENTOR(S) : Sutor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this

Twelfth Day of October, 2010

David J. Kappos
*Director of the United States Patent and Trademark Office*